US011984207B2

(12) United States Patent
Hasegawa

(10) Patent No.: US 11,984,207 B2
(45) Date of Patent: May 14, 2024

(54) MEDICAL DOCUMENT CREATION SUPPORT APPARATUS, METHOD, AND PROGRAM

(71) Applicant: FUJIFILM Corporation, Tokyo (JP)

(72) Inventor: Yu Hasegawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 346 days.

(21) Appl. No.: 17/485,478

(22) Filed: Sep. 26, 2021

(65) Prior Publication Data

US 2022/0013205 A1 Jan. 13, 2022

Related U.S. Application Data

(63) Continuation of application No. PCT/JP2020/005514, filed on Feb. 13, 2020.

(30) Foreign Application Priority Data

Apr. 4, 2019 (JP) ................................ 2019-071802

(51) Int. Cl.
*G16H 15/00* (2018.01)
*G06T 7/00* (2017.01)
*G16H 30/40* (2018.01)

(52) U.S. Cl.
CPC ........... *G16H 15/00* (2018.01); *G06T 7/0012* (2013.01); *G16H 30/40* (2018.01); *G06T 2207/10012* (2013.01); *G06T 2207/10072* (2013.01)

(58) Field of Classification Search
None
See application file for complete search history.

(56) References Cited

U.S. PATENT DOCUMENTS

2005/0069184 A1* 3/2005 Kasai .................... G06T 7/0012 382/128
2011/0075901 A1 3/2011 Nakamura
(Continued)

FOREIGN PATENT DOCUMENTS

EP 2478834 7/2012
JP H0731591 2/1995
(Continued)

OTHER PUBLICATIONS

Geoffrey D Rubin et al., "Pulmonary Nodules on Multi-Detector Row CT Scans: Performance Comparison of Radiologists and Computer-aided Detection," Jan. 2005, pp. 1-10. Published Online: https://doi.org/10.1148/radiol.2341040589.
(Continued)

*Primary Examiner* — Leon Flores
(74) *Attorney, Agent, or Firm* — JCIPRNET

(57) ABSTRACT

Provided are a medical document creation support apparatus, a method, and a non-transitory computer readable recording medium storing a program capable of efficiently correcting medical documents such as interpretation reports. A first display control unit displays a medical document including at least one of a plurality of findings indicating features related to abnormal shadows included in a medical image in a first display region on a display screen. A second display control unit displays a list of the plurality of findings in a second display region on the display screen so that each finding is correctable. A correction unit corrects the medical document according to a correction instruction for a designated finding in the list of the plurality of findings.

18 Claims, 15 Drawing Sheets

START
ST1 ACQUISITION OF INFORMATION
ST2 SWITCHING DISPLAY OF IMAGE
ST3 ABNORMAL SHADOW SELECTED? (NO / YES)
ST4 DISPLAY OF FIRST DISPLAY REGION
ST5 DISPLAY OF SECOND DISPLAY REGION
ST6 CORRECTION INSTRUCTION? (YES / NO)
ST7 CORRECTION OF INTERPRETATION REPORT
ST8 CANCEL BUTTON SELECTED? (YES / NO)
ST9 DISCARDING OF CORRECTIONS
ST10 CLOSE BUTTON SELECTED? (NO / YES)
ST11 UPDATE OF INFORMATION
ST12 TRANSMISSION OF INFORMATION
END

(56) References Cited

U.S. PATENT DOCUMENTS

| | | | |
|---|---|---|---|
| 2012/0054652 | A1 | 3/2012 | Kawagishi et al. |
| 2018/0166167 | A1 | 6/2018 | Kanada |

FOREIGN PATENT DOCUMENTS

| | | |
|---|---|---|
| JP | 2012053632 | 3/2012 |
| JP | 2012069089 | 4/2012 |
| JP | 2013039230 | 2/2013 |
| JP | 2018130408 | 8/2018 |

OTHER PUBLICATIONS

"International Search Report (Form PCT/ISA/210) of PCT/JP2020/005514," dated May 12, 2020, with English translation thereof, pp. 1-5.

"Written Opinion of the International Searching Authority (Form PCT/ISA/237)" of PCT/JP2020/005514, dated May 12, 2020, with English translation thereof, pp. 1-6.

"Search Report of Europe Counterpart Application", dated Apr. 25, 2022, p. 1-p. 8.

* cited by examiner 30
14
51
DT2
40
A2
50

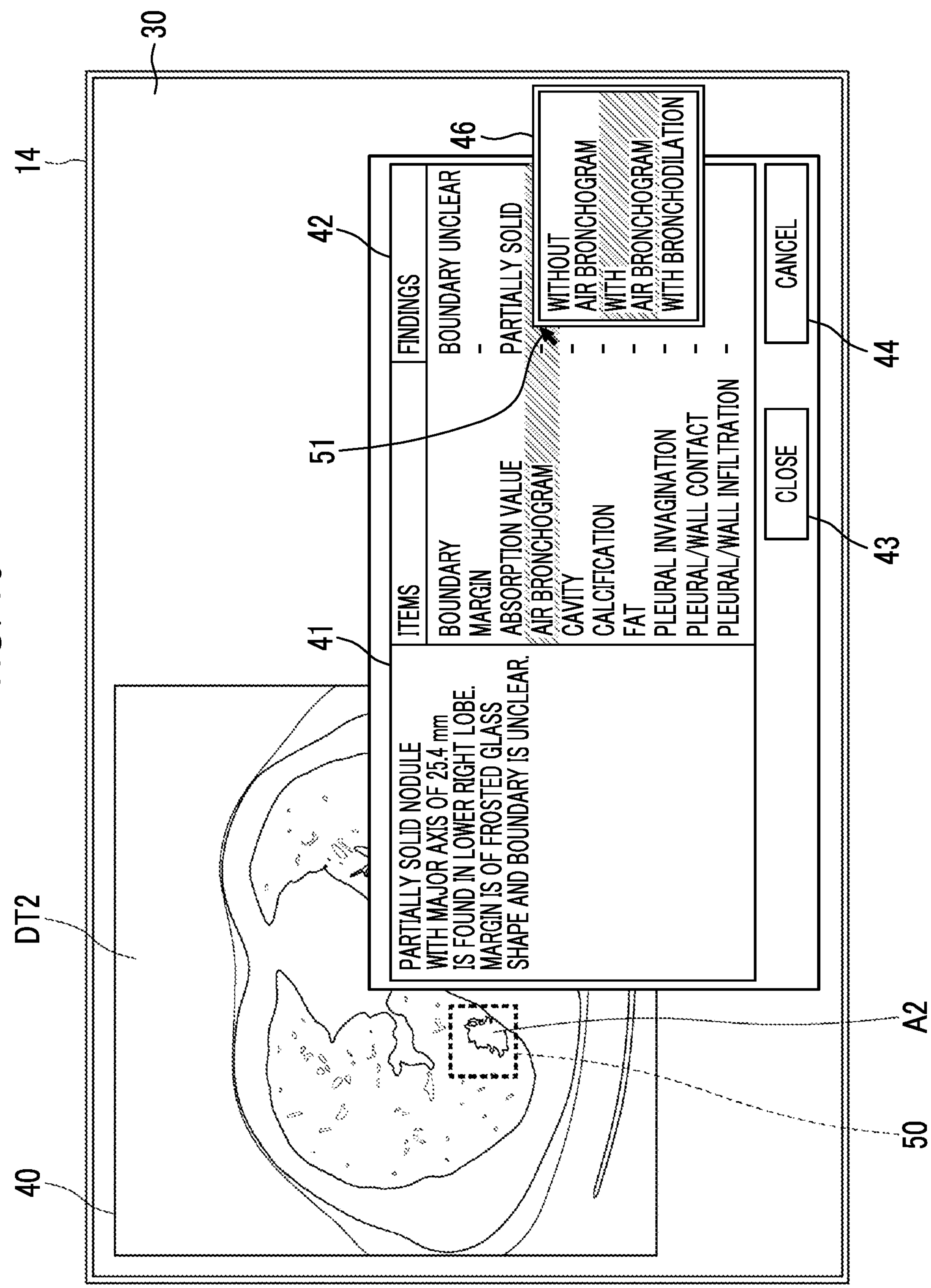
FIG. 10
14
30
DT2
40
41
42
46
51
43
44
A2
50
PARTIALLY SOLID NODULE
WITH MAJOR AXIS OF 25.4 mm
IS FOUND IN LOWER RIGHT LOBE.
MARGIN IS OF FROSTED GLASS
SHAPE AND BOUNDARY IS UNCLEAR.
ITEMS
BOUNDARY
MARGIN
ABSORPTION VALUE
AIR BRONCHOGRAM
CAVITY
CALCIFICATION
FAT
PLEURAL INVAGINATION
PLEURAL/WALL CONTACT
PLEURAL/WALL INFILTRATION
FINDINGS
BOUNDARY UNCLEAR
PARTIALLY SOLID
WITHOUT AIR BRONCHOGRAM
WITH AIR BRONCHOGRAM
WITH BRONCHODILATION
CLOSE
CANCEL 30
14
DT2
40
41
42
PARTIALLY SOLID NODULE WITH MAJOR AXIS OF 25.4 mm IS FOUND IN LOWER RIGHT LOBE. BOUNDARY IS UNCLEAR AND AIR BRONCHOGRAM IS FOUND INSIDE.
ITEMS
FINDINGS
BOUNDARY
BOUNDARY UNCLEAR
MARGIN
-
ABSORPTION VALUE
PARTIALLY SOLID
AIR BRONCHOGRAM
YES
CAVITY
-
CALCIFICATION
-
FAT
-
PLEURAL INVAGINATION
-
PLEURAL/WALL CONTACT
-
PLEURAL/WALL INFILTRATION
-
CLOSE
CANCEL
43
44
51
A2
50

30
14
41
SOLID TUMOR WITH MAJOR AXIS
OF 34.0 mm IS FOUND
IN UPPER LEFT LOBE.
AIR BRONCHOGRAM IS FOUND INSIDE
WITH SPICULA PLEURAL INVAGINATION
ON MARGIN.
THERE IS NO CALCIFICATION.
CLOSE
43
CORRECT
47
A1
50
51
DT1
40

MEDICAL DOCUMENT CREATION SUPPORT APPARATUS, METHOD, AND PROGRAM

CROSS-REFERENCE TO RELATED APPLICATIONS

This application is a Continuation of PCT International Application No. PCT/JP2020/005514 filed on Feb. 13, 2020, which claims priority under 35 U.S.C § 119(a) to Japanese Patent Application No. 2019-071802 filed on Apr. 4, 2019. Each of the above application(s) is hereby expressly incorporated by reference, in its entirety, into the present application.

BACKGROUND OF THE INVENTION

1. Field of the Invention

The present disclosure relates to a medical document creation support apparatus, a method, and a non-transitory computer readable recording medium storing a program that support creation of medical documents such as an interpretation report.

2. Description of the Related Art

In recent years, advances in medical apparatuses, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MRI images, and the like, appropriate treatment is being performed based on the specified result.

Further, there are some cases in which a medical image is analyzed by computer-aided diagnosis (CAD) using a discriminator that has been trained by deep learning or the like, regions, positions, volumes, and the like of lesions included in the medical image are extracted to acquire these as an analysis result (for example, see Pulmonary Nodules on Multi-Detector Row CT Scans: Performance Comparison of Radiologists and Computer-aided Detection, Rubin G D et al., 2005; 234: 274-283). In this way, the analysis result generated by the analysis process is saved in a database in association with examination information, such as a patient name, gender, age, and a modality which has acquired a medical image, and provided for diagnosis. In this case, a radiology technician or the like who has acquired a medical image decides a radiologist according to the medical image and informs the decided radiologist that the medical image and CAD analysis results are present. The radiologist interprets the medical image by referring to the distributed medical image and analysis result and creates an interpretation report, in his or her own interpretation terminal.

Meanwhile, with the improvement of the performance of the CT apparatus and the MRI apparatus described above, the number of medical images to be interpreted is also increasing. However, since the number of radiologists has not kept up with the number of medical images, it is desired to reduce the burden of the image interpretation work of the radiologists. Therefore, various methods have been proposed to support the creation of medical documents such as interpretation reports. For example, JP2013-39230A proposes a method of generating findings from CAD analysis results by using a discriminator trained to output findings of a lesion size, shape, and estimated disease name, or the like by inputting the CAD analysis results (see JP2013-39230A). In addition, a method of generating an interpretation report including the findings estimated in this way based on a fixed form is also proposed (see JP1995-31591A (JP-H7-31591A)). By automatically generating the interpretation report in this way, the burden on the radiologist in the case of creating the interpretation report can be reduced.

SUMMARY OF THE INVENTION

On the other hand, the findings included in the interpretation report automatically created by the methods described in JP2013-39230A and JP1995-31591A (JP-H7-31591A) may differ from the findings of the doctor who interpreted the image. In a case where the content of the interpretation report and the findings of the image examined by the doctor are different from each other as described above, it is necessary to correct the interpretation report. However, since the number of medical images to be interpreted is increasing as described above, it is desired to efficiently correct the interpretation report.

The present disclosure has been made in consideration of the above circumstances, and an object thereof is to efficiently correct medical documents such as interpretation reports.

A medical document creation support apparatus according to an aspect of the present disclosure comprises a first display control unit that displays a medical document including at least one of a plurality of findings indicating features related to abnormal shadows included in a medical image in a first display region on a display screen, a second display control unit that displays a list of the plurality of findings in a second display region on the display screen, which each finding is in a correctable manner, and a correction unit that corrects the medical document according to a correction instruction for a designated finding in the list of the plurality of findings.

In the medical document creation support apparatus according to the aspect of the present disclosure, the second display control unit may further display a list of correction candidates for the designated finding, and the correction unit may correct the medical document according to an instruction to select a desired correction candidate in the list of correction candidates.

In the medical document creation support apparatus according to the aspect of the present disclosure, the medical image may be a three-dimensional image including a plurality of tomographic images, the medical document creation support apparatus may further comprise an image display control unit that switches and displays the plurality of tomographic images on the display screen and highlights the abnormal shadow in a case where a tomographic image including the abnormal shadow is displayed during the switching display, the first display control unit may display the first display region in a case where the abnormal shadow is selected in the tomographic image being displayed, and the second display control unit may display the second display region in a case where the abnormal shadow is selected in the tomographic image being displayed.

In the medical document creation support apparatus according to the aspect of the present disclosure, the second display control unit may display the second display region according to an instruction to display the second display region.

The medical document creation support apparatus according to the aspect of the present disclosure may further comprise an image analysis unit that detects the abnormal shadow included in the medical image, a finding detection unit that detects the finding included in the abnormal shadow, and a document creation unit that creates the medical document based on the detected finding.

A medical document creation support method according to another aspect of the present disclosure comprises displaying a medical document including at least one of a plurality of findings indicating features related to abnormal shadows included in a medical image in a first display region on a display screen, displaying a list of the plurality of findings in a second display region on the display screen, which each finding is in a correctable manner, and correcting the medical document according to a correction instruction for a designated finding in the list of the plurality of findings.

In addition, the medical document creation support method according to the aspect of the present disclosure may be provided as a non-transitory computer readable recording medium storing a program for causing a computer to execute the method.

A medical document creation support apparatus according to another aspect of the present disclosure comprises a memory that stores instructions to be executed by a computer, and a processor configured to execute the stored instructions, and the processor executes the process of displaying a medical document including at least one of a plurality of findings indicating features related to abnormal shadows included in a medical image in a first display region on a display screen, displaying a list of the plurality of findings in a second display region on the display screen, which each finding is in a correctable manner, and correcting the medical document according to a correction instruction for a designated finding in the list of the plurality of findings.

According to the aspects of the present disclosure, it is possible to efficiently correct medical documents.

BRIEF DESCRIPTION OF THE DRAWINGS

FIG. 10 is a diagram showing a display screen in which a pull-down menu of correction candidates is displayed for a selected item.

DESCRIPTION OF THE PREFERRED EMBODIMENTS

Figure 1:
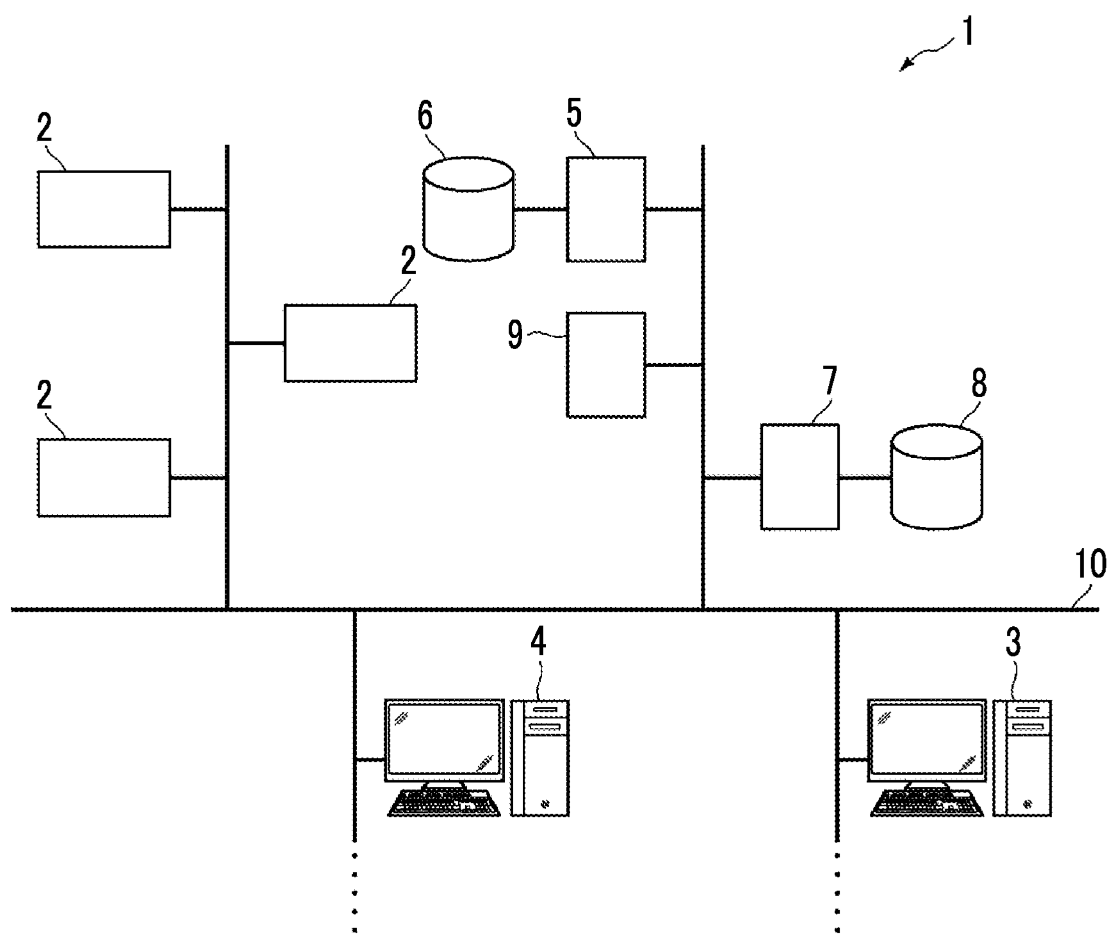
FIG. 1 is a diagram showing a schematic configuration of a medical information system to which a medical document creation support apparatus according to an embodiment of the present disclosure is applied.

Hereinafter, an embodiment of the present disclosure will be described with reference to the diagrams. FIG. 1 is a diagram showing a schematic configuration of a medical information system to which a medical document creation support apparatus according to an embodiment of the present disclosure is applied. A medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source. As shown in FIG. 1, the medical information system 1 is configured to include a plurality of modalities (imaging apparatuses) 2, a plurality of interpretation workstations (WS) 3 that are interpretation terminals, a medical department workstation (WS) 4, an image server 5, an image database 6, an interpretation report server 7, an interpretation report database 8, and an analysis server 9 that are communicably connected to each other through a wired or wireless network 10.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and installed on the computer from the recording medium. Alternatively, the application program is stored in a storage apparatus of a server computer connected to the network 10 or in a network storage in a state in which it can be accessed from the outside, and is downloaded and installed on the computer in response to a request.

The modality 2 is an apparatus that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. A medical image generated by the modality 2 is transmitted to the image server 5 and saved therein.

The interpretation WS 3 encompasses the medical document creation support apparatus according to the present embodiment. The configuration of the interpretation WS 3 will be described later.

The medical department WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical department WS 4, each process such as creating a medical record (electronic medical record) of a patient, requesting the image server 5 to view an image, displaying an image received from the image server 5, automatically detecting or highlighting a lesion-like portion in the image, requesting the interpretation report server 7 to view an interpretation report, and displaying the interpretation report received from the interpretation report server 7 is performed by executing a software program for each process.

The image server 5 is a general-purpose computer on which a software program that provides a function of a database management system (DBMS) is installed. The image server 5 comprises a storage in which the image database 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the modality 2, the image server 5 prepares the medical image in a format for a database and registers the medical image in the image database 6.

Image data of the medical image acquired by the modality 2 and accessory information are registered in the image database 6. The accessory information includes, for example, an image identification (ID) for identifying each medical image, a patient ID for identifying a subject, an examination ID for identifying an examination, a unique ID (UID: unique identification) allocated for each medical image, examination date and examination time at which a medical image is generated, the type of modality used in an examination for acquiring a medical image, patient information such as the name, age, and gender of a patient, an examination part (imaging part), imaging information (an imaging protocol, an imaging sequence, an imaging method, imaging conditions, the use of a contrast medium, and the like), and information such as a series number or a collection number when a plurality of medical images are acquired in one examination.

In addition, in a case where a viewing request from the interpretation WS 3 is received through the network 10, the image server 5 searches for a medical image registered in the image database 6 and transmits the searched medical image to the interpretation WS 3 that is a request source.

The interpretation report server 7 incorporates a software program for providing a function of a database management system to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and confidence of the findings, is recorded.

The analysis server 9 is a computer on which a software program that provides a function of analyzing a medical image by CAD or the like to detect abnormal shadows such as lesions, a software program that provides a function of detecting findings about abnormal shadows, and a software program that provides a function of creating an interpretation report using the CAD analysis results and the detection results of findings are installed. A medical image analysis process, a finding detection process, and an interpretation report creation process on the analysis server 9 are performed according to instructions from the medical department WS 4 or the interpretation WS 3. In a case where the analysis server 9 receives instructions for the medical image analysis process, the finding detection process, and the interpretation report creation process, the analysis server 9 acquires the medical image to be processed from the image server 5. Then, the analysis server 9 analyzes the acquired medical image, detects the findings, further creates an interpretation report, transmits the created interpretation report to the interpretation report server 7, and registers the interpretation report. In this case, a request to register the interpretation report is made from the analysis server 9. In the present embodiment, along with the interpretation report, findings detected by the finding detection process and finding information including the information on the position and size of the abnormal shadow are also transmitted to the interpretation report server 7.

As the analysis process by CAD, for example, the method described in Pulmonary Nodules on Multi-Detector Row CT Scans: Performance Comparison of Radiologists and Computer-aided Detection, Rubin G D et al., 2005; 234: 274-283 can be used. Further, as the method of generating findings from the analysis process by CAD and creating an interpretation report from the findings, for example, the methods described in JP2013-39230A and JP1995-31591A (JP-H7-31591A) can be used. However, the analysis process by CAD and the method of creating an interpretation report are not limited thereto.

Further, in the present embodiment, the medical image is a CT image consisting of a plurality of tomographic images with the diagnosis target as the lung, abnormal shadows contained in the lungs by CAD are detected, findings about the detected abnormal shadows are detected, the detected findings are used, and thereby an interpretation report on the abnormal shadows contained in the lungs is created as a medical document. The image is not limited to the CT image, and may be an MRI image. Further, it may be a simple two-dimensional image acquired by a simple X-ray imaging apparatus.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Hereinafter, the interpretation WS 3 according to the present embodiment will be described in detail. The interpretation WS 3 is a computer used by a radiologist of a medical image to interpret the medical image and create an interpretation report, and is configured to include a processing apparatus, a display apparatus such as a display, and an input apparatus such as a keyboard and a mouse. In the interpretation WS 3, each process such as requesting the image server 5 to view a medical image, various kinds of image processing on the medical image received from the image server 5, displaying the medical image, an analysis process on the medical image, highlighting the medical image based on the analysis result, creating the interpretation report based on the analysis result, supporting the creation of an interpretation report, requesting the interpretation report server 7 to register and view the interpretation report, and displaying the interpretation report received from the interpretation report server 7 is performed by executing a software program for each process. Note that, in these processes, processes other than those performed by the medical document creation support apparatus according to the present embodiment are performed by a well-known software program, and therefore the detailed description thereof will be omitted here. In addition, processes other than the processes performed by the medical document creation support apparatus according to the present embodiment may not be performed in the interpretation WS 3, and a computer that performs the processes may be separately connected to the network 10, and in response to a processing request from the interpretation WS 3, the requested process may be performed by the computer.

The interpretation WS 3 encompasses the medical document creation support apparatus according to the present embodiment. Therefore, the medical document creation support program according to the present embodiment is installed on the interpretation WS 3. The medical document creation support program is stored in the storage apparatus of the server computer connected to the network or in the network storage in a state in which it can be accessed from the outside, and is downloaded and installed on the interpretation WS 3 in response to a request. Alternatively, the medical document creation support program is recorded on a recording medium such as a DVD or a CD-ROM, distributed, and installed on the interpretation WS 3 from the recording medium.

Figure 2:
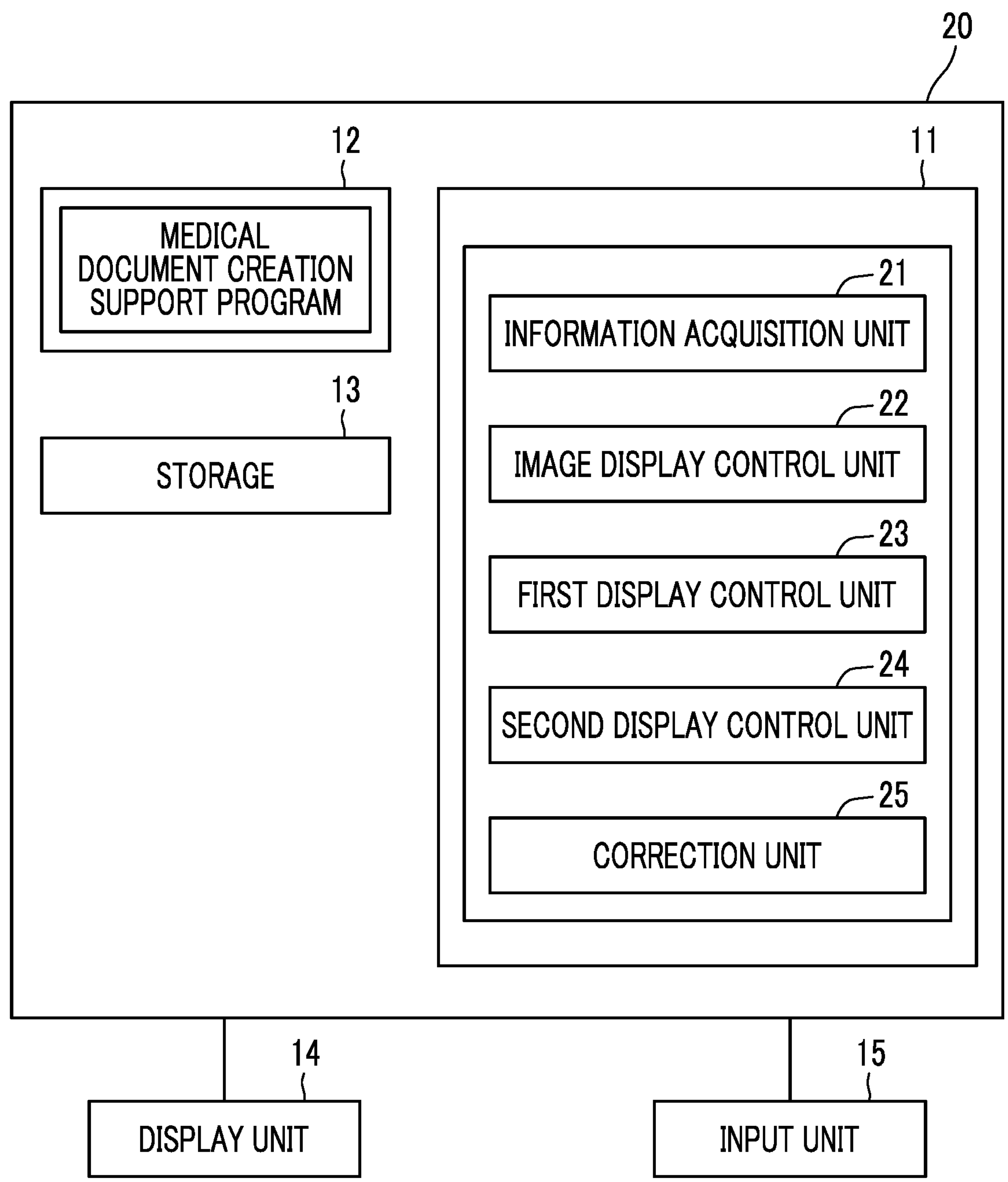
FIG. 2 is a diagram showing a schematic configuration of the medical document creation support apparatus according to the present embodiment.

FIG. 2 is a diagram showing a schematic configuration of the medical document creation support apparatus according to the present embodiment, which is realized by installing the medical document creation support program. As shown in FIG. 2, a medical document creation support apparatus 20 comprises a central processing unit (CPU) 11, a memory 12, and a storage 13 as the configuration of a standard computer. A display apparatus (hereinafter, referred to as a “display unit”) 14, such as a liquid crystal display, and an input apparatus (hereinafter, referred to as an “input unit”) 15, such as a keyboard and a mouse, are connected to the medical document creation support apparatus 20.

The storage 13 consists of a storage device, such as a hard disk or a solid state drive (SSD). The storage 13 stores various kinds of information including medical images and information necessary for processing of the medical document creation support apparatus 20, which are acquired from the image server 5 through the network 10.

Further, the memory 12 stores a medical document creation support program. The medical document creation support program defines, as processes to be executed by the CPU 11, an information acquisition process of acquiring an interpretation report, and the above-mentioned finding information and medical image, an image display control process of switching and displaying a plurality of tomographic images constituting the medical image on a display screen, and highlighting an abnormal shadow in a case where a tomographic image including the abnormal shadow is displayed during the switching display, a first display control process of displaying an interpretation report including at least one of a plurality of findings indicating features related to abnormal shadows included in the medical image in a first display region on the display screen, a second display control process of displaying a list of the plurality of findings in a second display region on the display screen so that each finding can be corrected, and a correction process of correcting the interpretation report according to a correction instruction for a designated finding in the list of findings.

The computer functions as an information acquisition unit 21, an image display control unit 22, a first display control unit 23, a second display control unit 24, and a correction unit 25 by the CPU 11 executing these processes according to the medical document creation support program.

The information acquisition unit 21 consists of an interface connected to the network 10, and acquires an interpretation report and finding information from the interpretation report server 7 according to an instruction from an input unit 15 by a radiologist who is an operator. Further, in order to check the contents of the interpretation report, the medical image for which the interpretation report is created is acquired from the image server 5.

Figure 3:
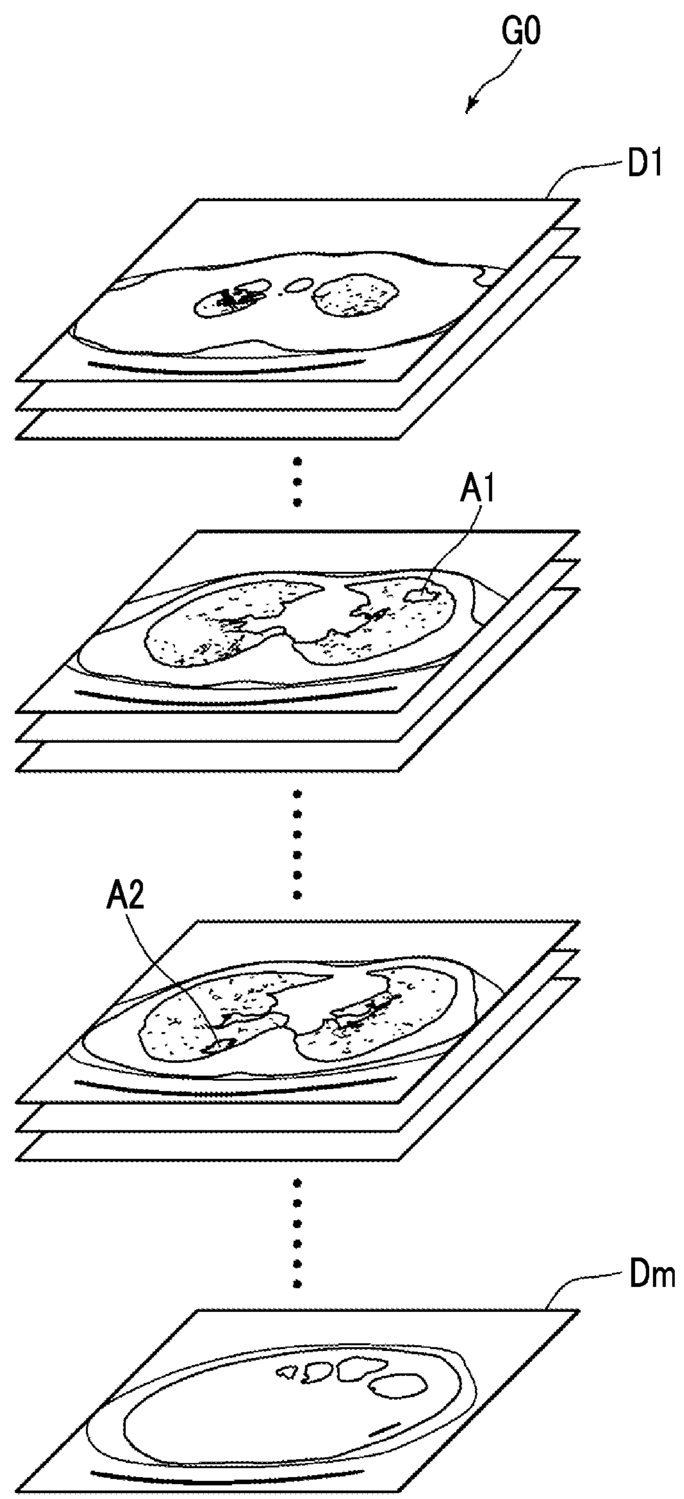
FIG. 3 is a diagram schematically showing a medical image.

The image display control unit 22 displays a medical image G0 on the display screen displayed on a display unit 14 according to an instruction from the input unit 15 by the operator. In this case, a plurality of tomographic images constituting the medical image G0 are sequentially switched and displayed on the display screen according to the instruction of the switching display from the input unit 15 by the operator. FIG. 3 is a diagram schematically showing the medical image G0. In the present embodiment, the medical image G0 is a three-dimensional image consisting of m tomographic images D1 to Dm, and as a result of analysis by the analysis server 9, it is assumed that abnormal shadows A1 and A2 are specified in, for example, two places.

Here, in the present embodiment, the finding information acquired by the information acquisition unit 21 includes information on the size and position of the abnormal shadow. In a case where a tomographic image including the abnormal shadow is displayed during the switching display of a tomographic image Dk (k=1 to m), the image display control unit 22 specifies the size and position of the abnormal shadow included in the tomographic image based on the finding information, and highlights the specified abnormal shadow. The size of the abnormal shadow can be the vertical and horizontal sizes of the abnormal shadow in each of the tomographic images D1 to Dm. Further, since the abnormal shadow has a shape close to a circle, the diameter when the abnormal shadow is approximated to a circle may be used as the size. The position of the abnormal shadow can be, for example, the centroid position of the abnormal shadow in each tomographic image.

Figure 4:
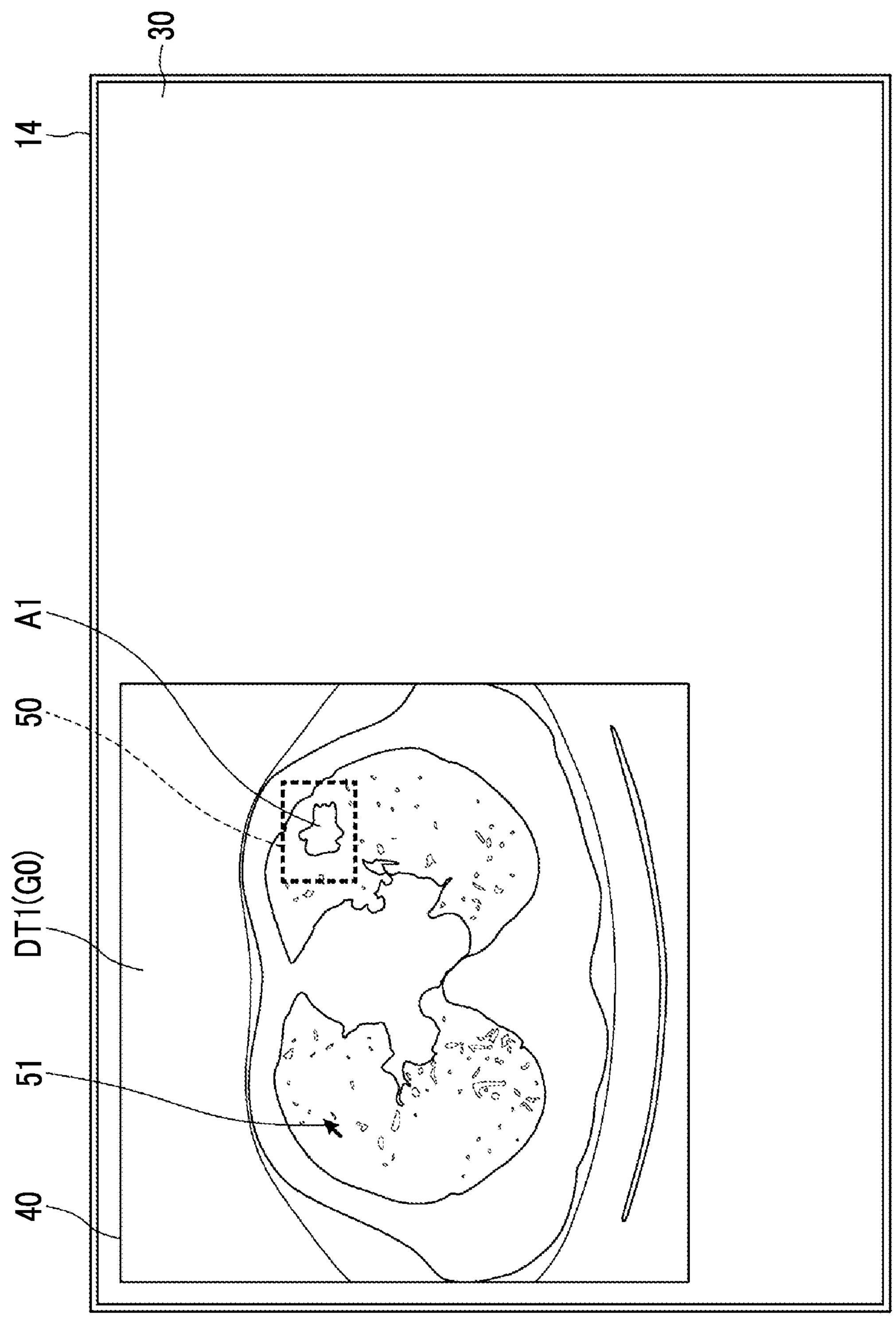
FIG. 4 is a diagram showing a display screen of a medical image.

FIG. 4 is a diagram showing a display screen of a medical image. As shown in FIG. 4, a display screen 30 includes an image display region 40, and the medical image G0 is displayed in the image display region 40. The image display control unit 22 switches and displays a plurality of tomographic images in the image display region 40 according to the instruction of the switching display from the input unit 15 by the operator. Then, in a case where a tomographic image DT1 including the abnormal shadow A1 in the medical image G0 is displayed in the image display region, the image display control unit 22 highlights the abnormal shadow A1. In FIG. 4, the abnormal shadow A1 is highlighted by surrounding the abnormal shadow A1 with a rectangular region 50 having a broken line corresponding to the position and size of the abnormal shadow A1 included in the finding information. The rectangular region 50 is not limited to the broken line, and may be another line type such as a solid line. The highlighting is not limited thereto, and the abnormal shadow A1 may be marked with an arrow or the like, or the line in the region surrounding the abnormal shadow A1 may be colored.

A cursor 51 is displayed on the display unit 14. The operator can operate the input unit 15 to move the cursor 51 to a desired position on the display screen 30.

Figure 5:
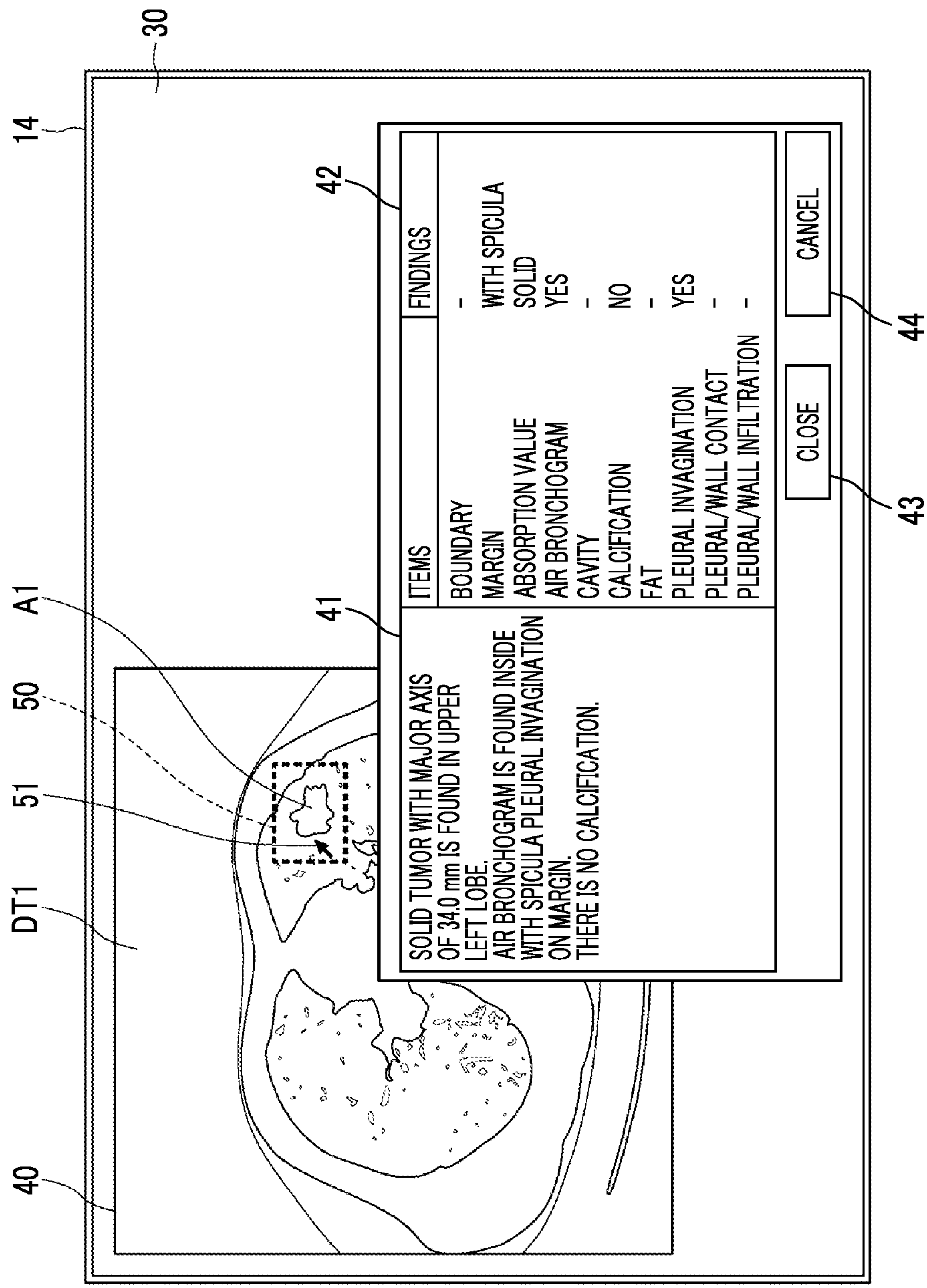
FIG. 5 is a diagram showing a display screen on which a first display region and a second display region are displayed.

The first display control unit 23 displays a first display region 41 on the display screen 30, and displays an interpretation report including at least one of a plurality of findings indicating features related to abnormal shadows included in the medical image G0 in the first display region 41 (see FIG. 5).

The second display control unit 24 displays a second display region on the display screen 30, and displays a list of the plurality of findings in the second display region so that each finding can be corrected (see FIG. 5).

In the present embodiment, in the tomographic image DT1 displayed in the image display region 40 as shown in FIG. 4, in a case where the operator uses the input unit 15 to select the rectangular region 50 surrounding the abnormal shadow A1 with the cursor 51, as shown in FIG. 5, the first display control unit 23 and the second display control unit 24 display the first display region 41 and the second display region 42 side by side on the display screen 30. The first display control unit 23 displays an interpretation report of "A solid tumor with a major axis of 34.0 mm is found in the upper left lobe. An air bronchogram is found inside with a spicula pleural invagination on the margin. There is no calcification." in the first display region 41. The second display control unit 24 displays a list of findings based on the finding information detected by the analysis server 9 in the second display region 42 in a correctable manner. The list of findings includes items of the findings and the findings corresponding to the items. Items of the findings include, but are not limited to, a boundary, a margin, an absorption value, an air bronchogram, a cavity, a calcification, fat, pleural invagination, pleural/wall contact, and pleural/wall infiltration. Further, in FIG. 5, the finding of the margin is "with spicula", the finding of the absorption value is "solid", the finding of the air bronchogram is "yes", the finding of the calcification is "no", and the finding of the pleural invagination is "yes". For the findings of items other than these, "-" indicating that the findings were not detected is shown.

Further, a close button 43 and a cancel button 44 are displayed at the lower part of the second display region 42. The close button 43 and the cancel button 44 will be described later.

The operator interprets the tomographic image displayed in the image display region and determines whether or not the interpretation report displayed in the first display region 41 needs to be corrected. In a case where the correction is not necessary, the operator selects the close button 43 or the cancel button 44 to close the first display region 41 and the second display region 42.

Figure 6:
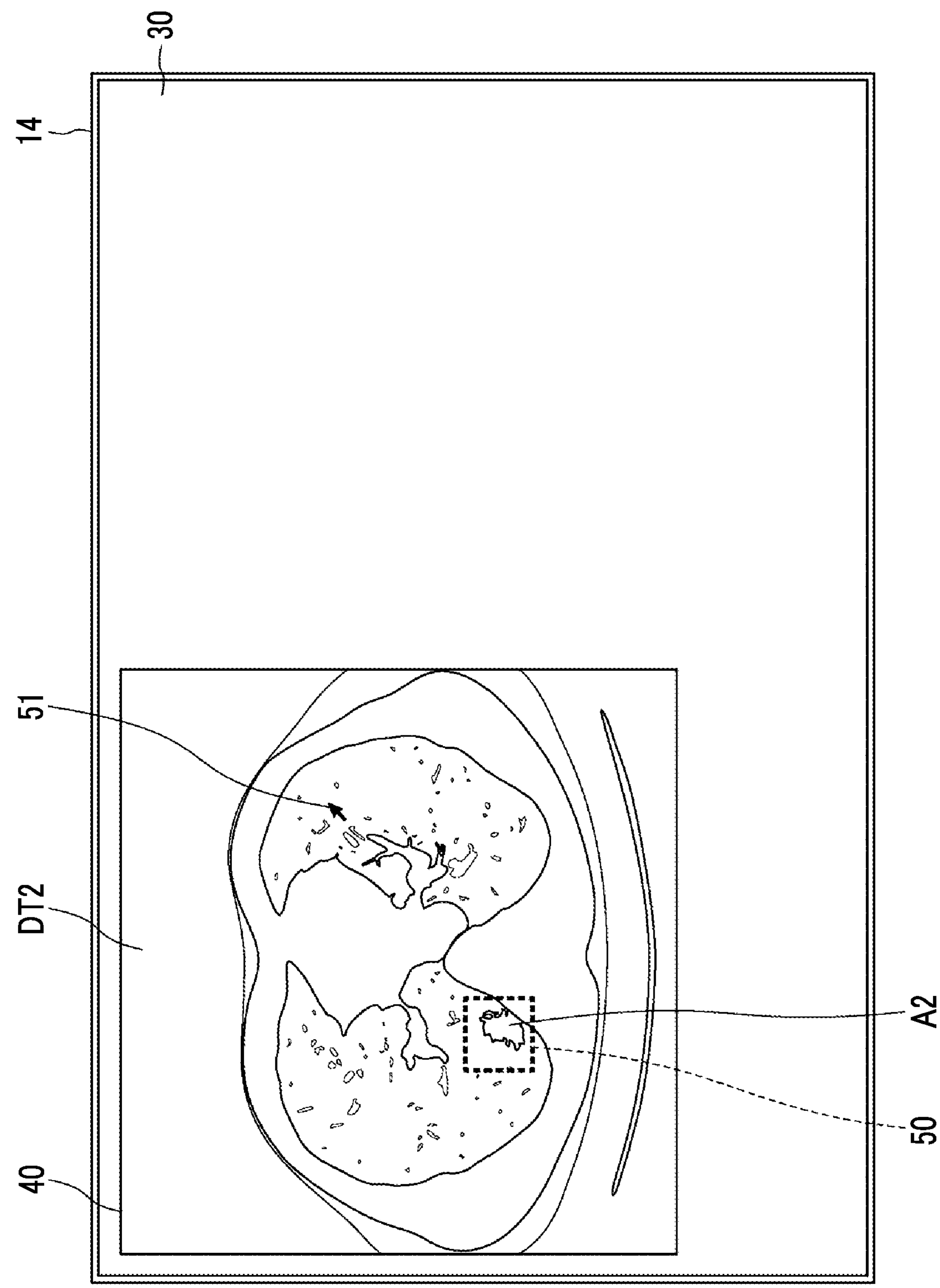
FIG. 6 is a diagram showing an example of a display screen of a medical image.

In a case where the correction is not necessary, the operator gives an instruction to the image display control unit 22 using the input unit 15, and continuously switches and displays the tomographic images in the image display region 40. Thereby, as shown in FIG. 6, a tomographic image DT2 including the abnormal shadow A2 different from the abnormal shadow A1 can be displayed in the image display region 40. The image display control unit 22 highlights the abnormal shadow A2 in the tomographic image DT2 by surrounding the abnormal shadow A2 with the rectangular region 50 in the same manner as the tomographic image DT1.

Figure 7:
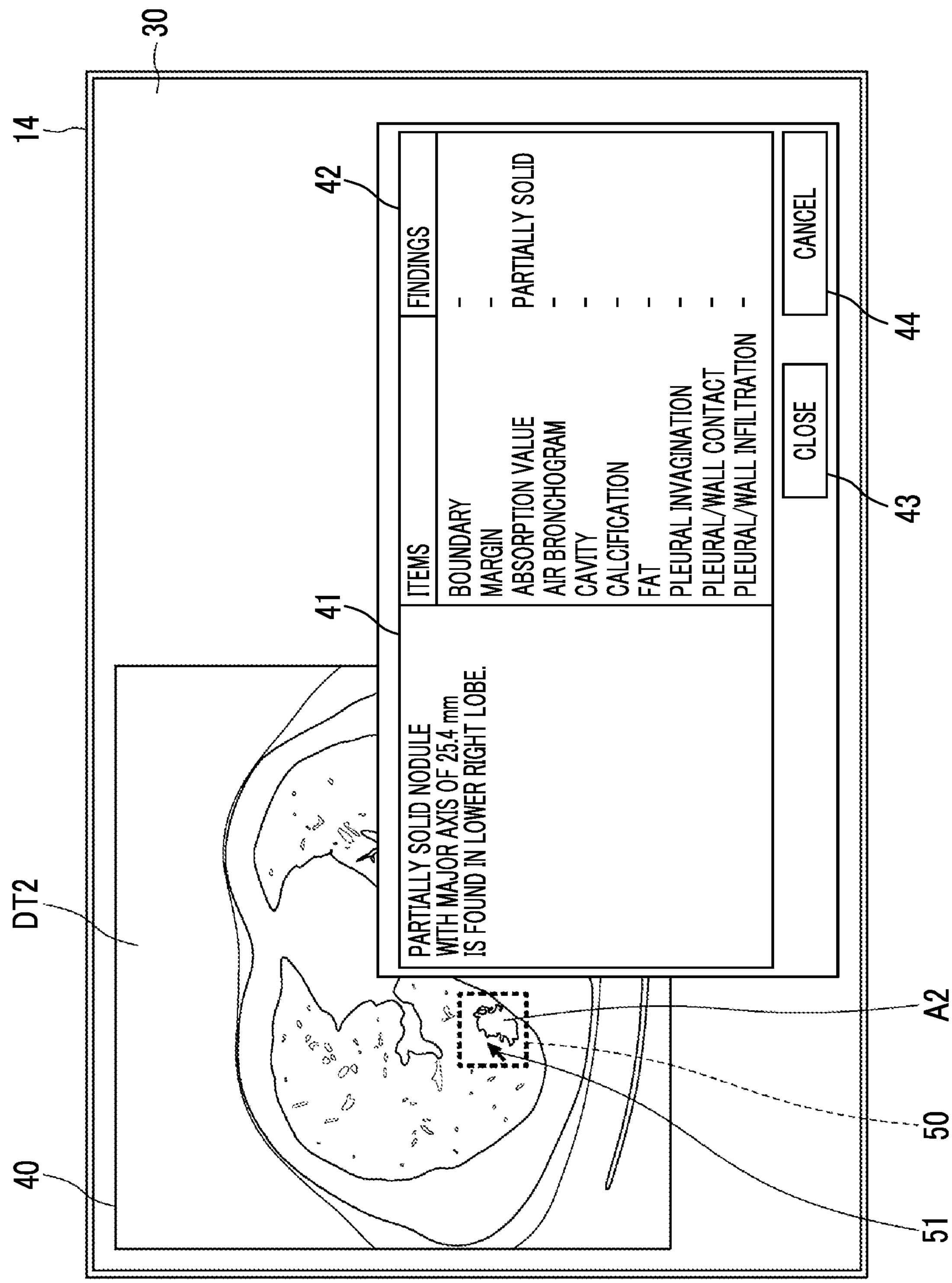
FIG. 7 is a diagram showing a display screen on which the first and second display regions are displayed.

In a case where the operator uses the input unit 15 to select the rectangular region 50 surrounding the abnormal shadow A2 with the cursor 51, as shown in FIG. 7, the first display control unit 23 and the second display control unit 24 display the first display region 41 and the second display region 42 side by side on the display screen 30. The first display control unit 23 displays an interpretation report of "A partially solid nodule with a major axis of 25.4 mm is found in the lower right lobe." in the first display region 41. The second display control unit 24 displays a list of findings based on the finding information in the second display region 42 in a correctable manner. In FIG. 7, the finding of the absorption value in the second display region 42 is "partially solid".

Figure 8:
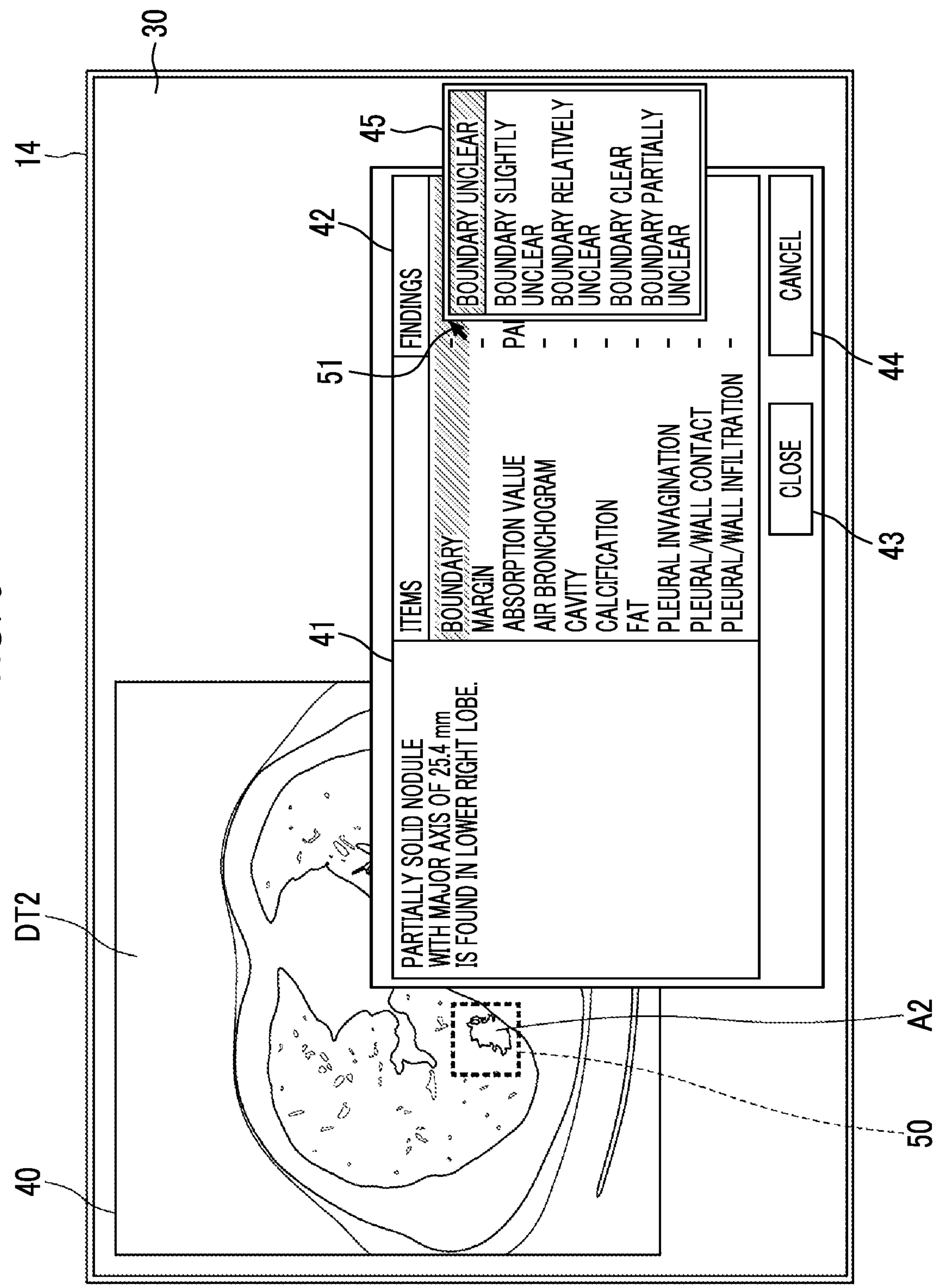
FIG. 8 is a diagram showing a display screen in which a pull-down menu of correction candidates is displayed for a selected item.

The operator interprets the tomographic image displayed in the image display region and determines whether or not the interpretation report displayed in the first display region 41 needs to be corrected. In a case where the correction is necessary, the operator selects the item for which correction is desired with the cursor 51 in the list of findings displayed in the second display region 42. The second display control unit 24 highlights the selected item. Further, the second display control unit 24 displays a pull-down menu of correction candidates for the selected item. FIG. 8 is a diagram showing a display screen in which a pull-down menu 45 of correction candidates is displayed for the selected item. As shown in FIG. 8, in the second display region 42, the item of "boundary" is selected by the cursor 51. In FIG. 8, the highlighting is shown by adding diagonal lines. In a case where an item is selected, the second display control unit 24 displays the pull-down menu 45 of correction candidates corresponding to the selected item. The pull-down menu 45 displays the findings corresponding to the selected item of "boundary". In FIG. 8, the findings of "boundary unclear", "boundary slightly unclear", "boundary relatively unclear", "boundary clear" and "boundary partially unclear" are displayed.

The operator can select a desired finding from the correction candidates by moving the cursor 51 in the pull-down menu 45 of the correction candidate. The second display control unit 24 highlights the selected finding. In FIG. 8, "boundary unclear" is selected.

The correction unit 25 corrects the interpretation report according to the correction instruction for the designated finding in the list of findings displayed in the second display region 42. For this purpose, the correction unit 25 has a trained model trained to create a sentence using the corrected findings. The trained model consists of, for example, a convolutional neural network (CNN) in which deep learning has been performed. However, in addition to CNN, a support vector machine (SVM), a deep neural network (DNN), a recurrent neural network (RNN), and the like can be used.

Figure 9:
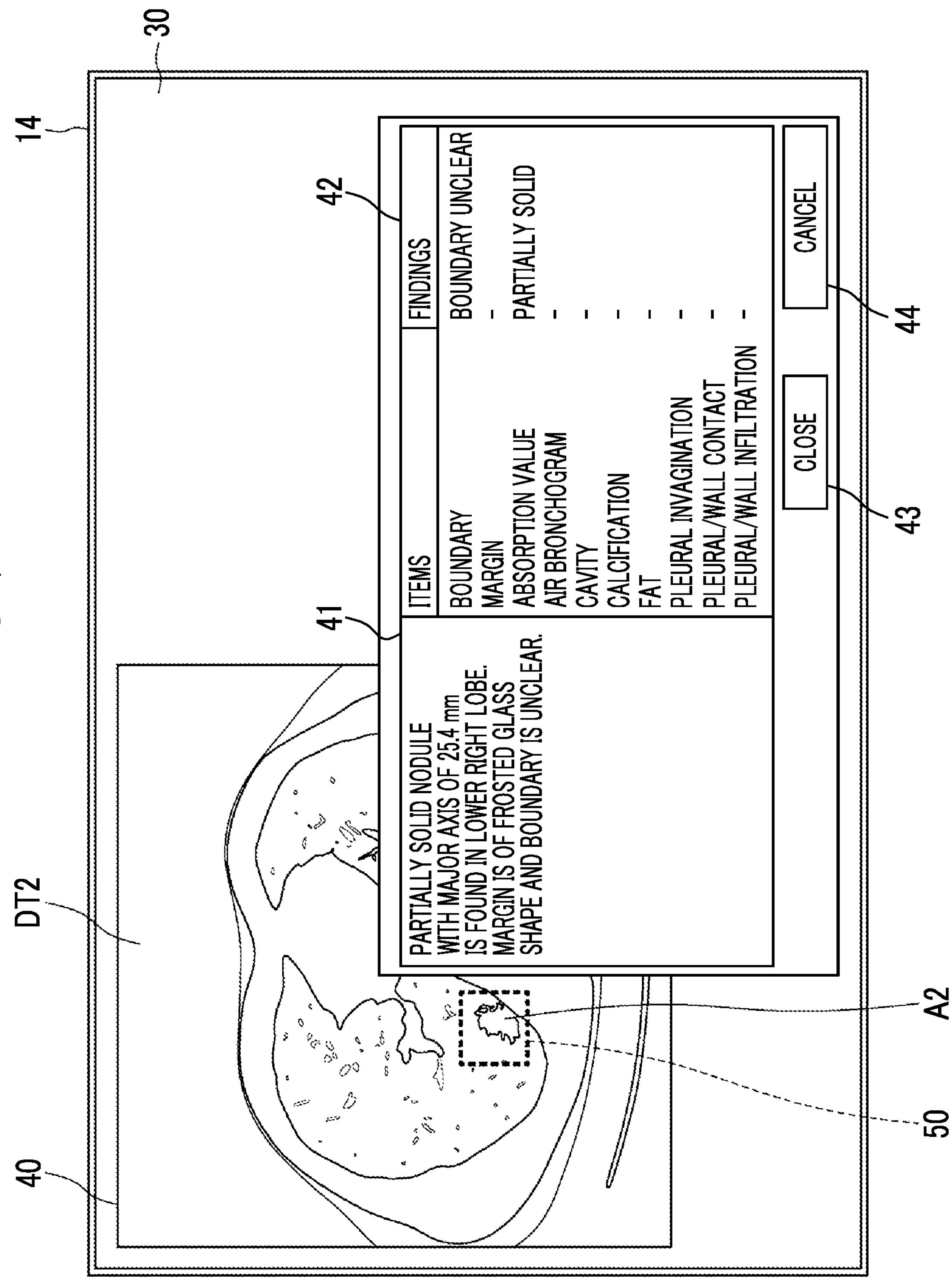
FIG. 9 is a diagram showing a display screen in which a finding has been corrected.

In a case where the finding is corrected in the second display region 42, the correction unit 25 generates a finding sentence from the corrected finding. For example, as shown in FIG. 8, in a case where the item of the boundary is corrected to be "boundary unclear", a finding sentence "The margin is of frosted glass shape and the boundary is unclear." is generated. The first display control unit 23 displays the generated finding sentence in the first display region 41. FIG. 9 is a diagram showing a display screen in which the finding has been corrected. On the display screen 30 shown in FIG. 9, as compared with FIG. 7, the finding of the boundary in the second display region 42 is "boundary unclear", and in the interpretation report displayed in the first display region 41, the finding sentence "The margin is of frosted glass shape and the boundary is unclear." is added.

In a case where the correction is further necessary, the operator further selects the item for which correction is desired with the cursor 51. Thereby, the second display control unit 24 displays a pull-down menu of correction candidates for the findings for the selected item. FIG. 10 shows a state in which a pull-down menu 46 of correction candidates is displayed for the further selected item. As shown in FIG. 10, in the second display region 42, the item of "air bronchogram" is selected by the cursor 51. The second display control unit 24 displays the pull-down menu 46 of correction candidates in a case where the item is selected. In the pull-down menu 46 of the correction candidate, the findings corresponding to the selected item of "air bronchogram" are displayed. In FIG. 10, the findings of "with air bronchogram", "without air bronchogram", and "with bronchodilation" are displayed.

Figure 11:
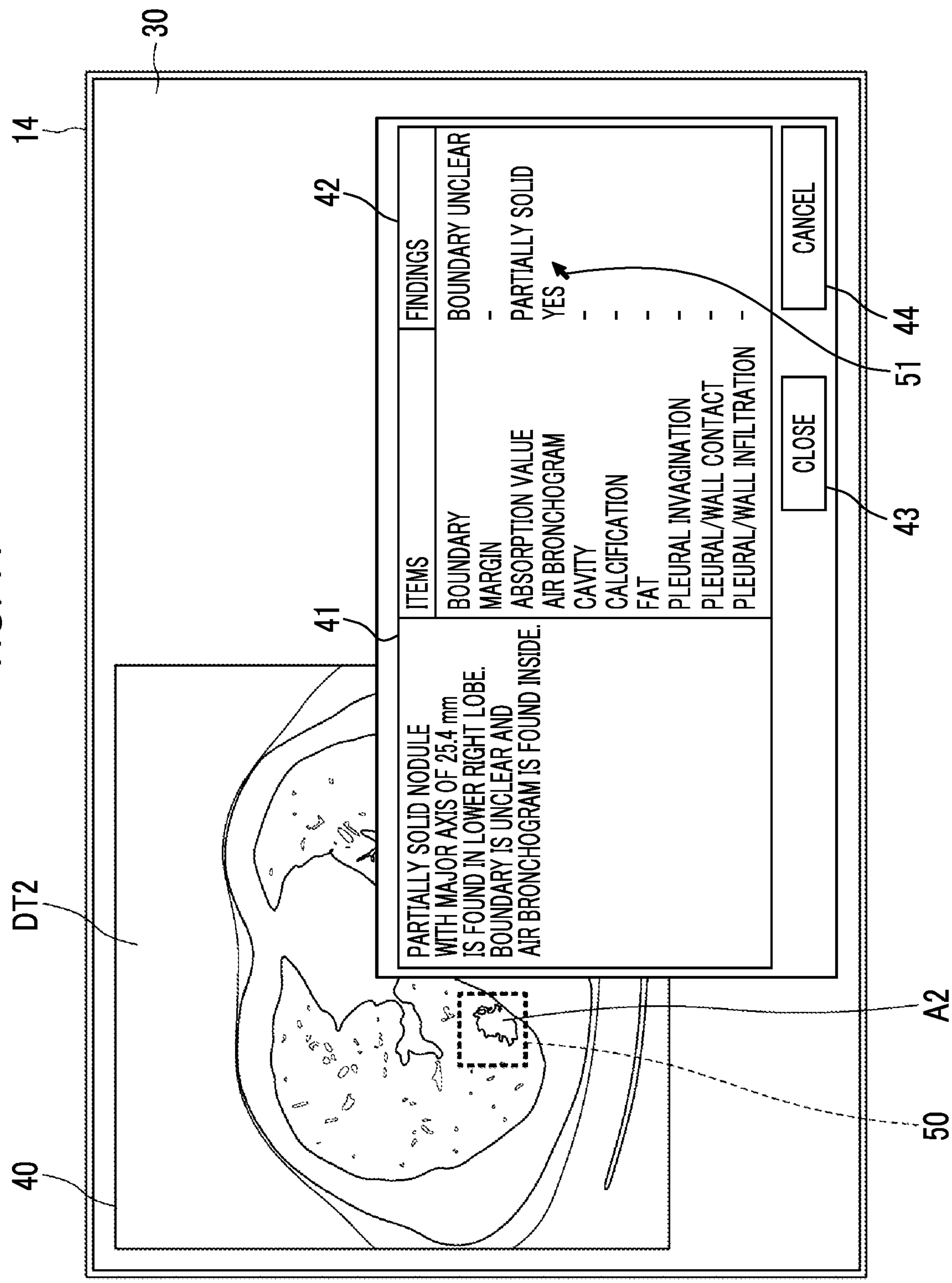
FIG. 11 is a diagram showing a display screen in which a finding has been corrected.

The operator can select a desired finding from the correction candidates by moving the cursor 51 in the pull-down menu 46. The second display control unit 24 highlights the selected finding. In FIG. 10, "with air bronchogram" is selected. Thereby, the correction unit 25 corrects the finding sentence "The margin is of frosted glass shape and the boundary is unclear." included in the interpretation report displayed in the first display region 41 to a finding sentence "The boundary is unclear and an air bronchogram is found inside.". FIG. 11 is a diagram showing a display screen in which the finding has been further corrected. On the display screen 30 shown in FIG. 11, as compared with FIG. 9, the finding of the air bronchogram in the second display region 42 is "yes", and the finding sentence "The margin is of frosted glass shape and the boundary is unclear." in the interpretation report displayed in the first display region 41 is corrected to the finding sentence "The boundary is unclear and an air bronchogram is found inside.".

Figure 12:
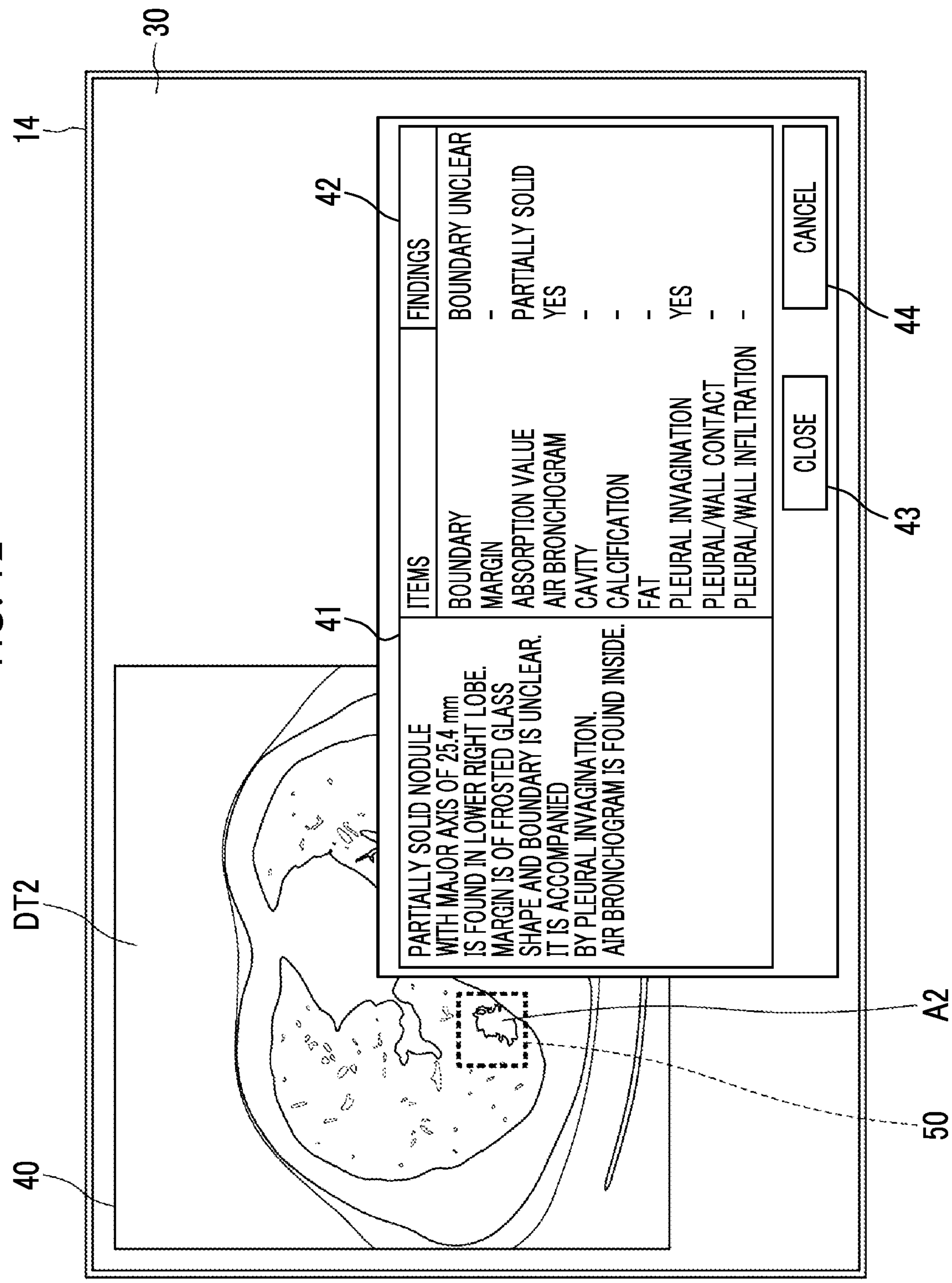
FIG. 12 is a diagram showing a correction screen in which correction is completed.

The operator corrects the findings desired to be corrected in the same manner as described above, and corrects the interpretation report. Thereby, the correction of the interpretation report is finally completed as shown in FIG. 12. The corrected interpretation report has been corrected to "A partially solid nodule with a major axis of 25.4 mm is found in the lower right lobe. The margin is of frosted glass shape and the boundary is unclear. It is accompanied by pleural invagination. An air bronchogram is found inside.". In addition to the "absorption value", the findings of the items "boundary", "air bronchogram", and "pleural invagination" are added to the list of findings.

The operator selects the close button 43 in a case where the correction of the interpretation report is completed. Thereby, the correction unit 25 updates the interpretation report and the finding information in order to reflect the correction contents, and transmits the updated interpretation report and finding information to the interpretation report server 7. In the interpretation report server 7, the saved interpretation report and finding information are updated by the updated interpretation report and the updated finding information. Further, in the case of re-correcting, the operator selects the cancel button 44. This cancels the correction operation and discards the corrections made so far. By selecting the rectangular region 50 again, the operator can display the first display region 41 and the second display region 42, and correct the interpretation report and the finding information.

The close button 43 and the cancel button 44 may be displayed by the correction unit 25, but may be performed by the first display control unit 23 or by the second display control unit 24.

Figure 13:
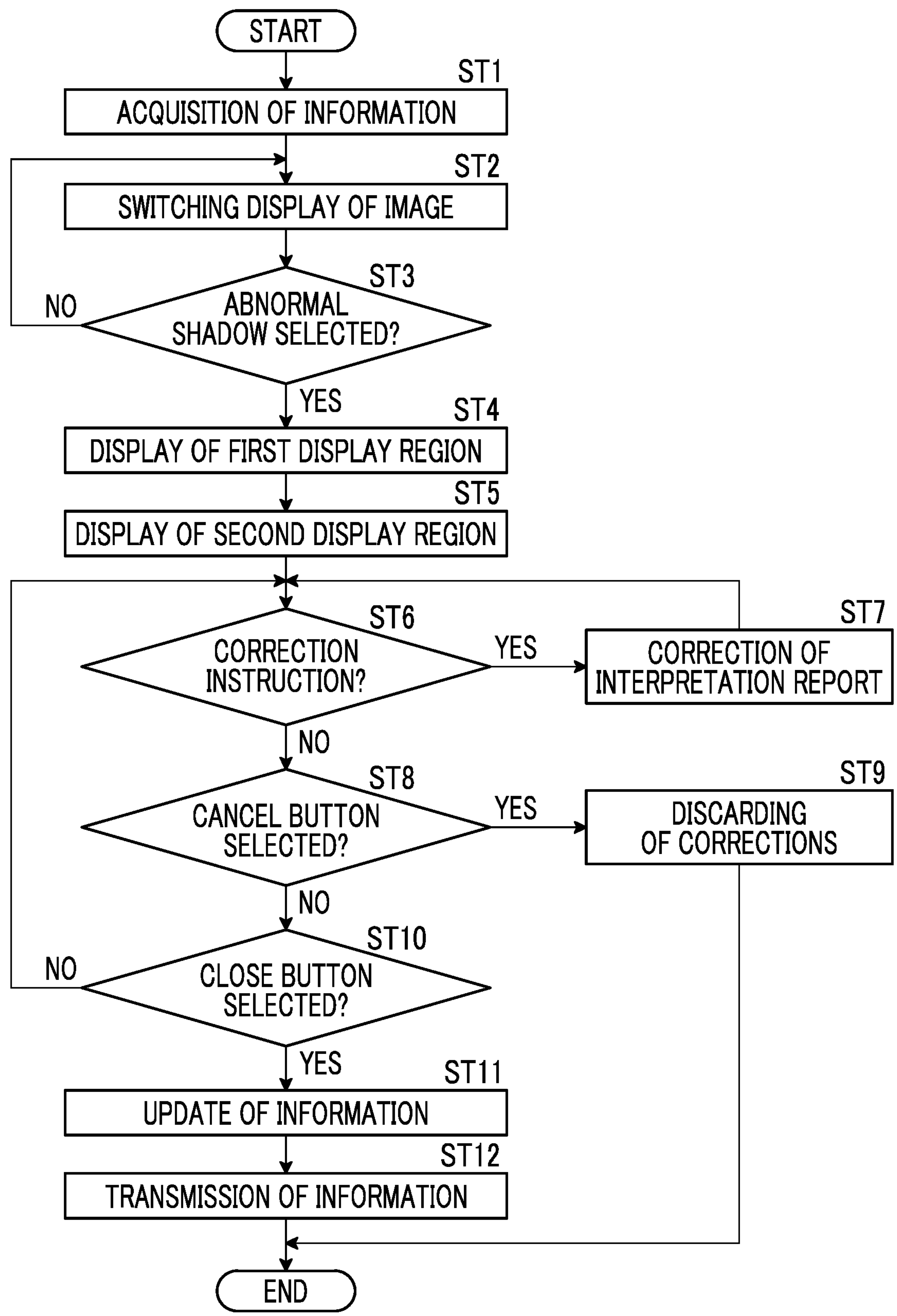
FIG. 13 is a flowchart showing a process performed in the present embodiment.

Next, a process performed in the present embodiment will be described. FIG. 13 is a flowchart showing a process performed in the present embodiment. The process is started in a case where the operator gives an instruction to interpret the medical image from the input unit 15, and the information acquisition unit 21 acquires the medical image G0 from the image server 5 and acquires the interpretation report and the finding information from the interpretation report server 7 (acquisition of information; step ST1). Then, the image display control unit 22 displays the medical image on the display screen 30 so that it can be switched and displayed (switching display of an image; step ST2).

The image display control unit 22 starts monitoring whether or not an abnormal shadow is selected by selecting a rectangular region included in the displayed tomographic image (step ST3). In a case where the rectangular region is selected (step ST3: YES), the first display control unit 23 displays the first display region 41 on the display screen 30 (step ST4), and the second display control unit 24 displays the second display region 42 on the display screen 30 (step ST5). As described above, the interpretation report is displayed in the first display region 41, and the list of findings is displayed in the second display region 42.

The correction unit 25 determines whether or not there is an instruction to correct the finding information using the second display control unit 24 (step ST6). In a case where step ST6 is affirmative, the correction unit 25 corrects the interpretation report according to the corrected findings (step ST7), and returns to step ST6. In a case where step ST6 is negative, the correction unit 25 determines whether or not the cancel button 44 has been selected (step ST8). In a case where step ST8 is affirmative, the corrections made so far are discarded (step ST9), and the process ends. In a case where step ST8 is negative, the correction unit 25 determines whether or not the close button 43 has been selected (step ST10). In a case where step ST10 is negative, the process returns to step ST6, and the processes after step ST6 are repeated. In a case where step ST10 is affirmative, the correction unit 25 updates the interpretation report and the finding information with the corrected contents (update of information; step ST11), the updated interpretation report and finding information are transmitted to the interpretation report server 7 (transmission of information; step ST12), and the process ends.

In this way, in the present embodiment, the interpretation report including at least one of the plurality of findings indicating the features related to the abnormal shadow included in the medical image G0 is displayed in the first display region 41, the list of the findings is displayed in the second display region 42 in a correctable manner, and the interpretation report is corrected according to a correction instruction for a designated finding in the list of the findings. Therefore, in a case where the operator performs the work of correcting the findings in the second display region 42, the interpretation report is corrected. Therefore, according to the present embodiment, the interpretation report can be efficiently corrected.

Figure 14:
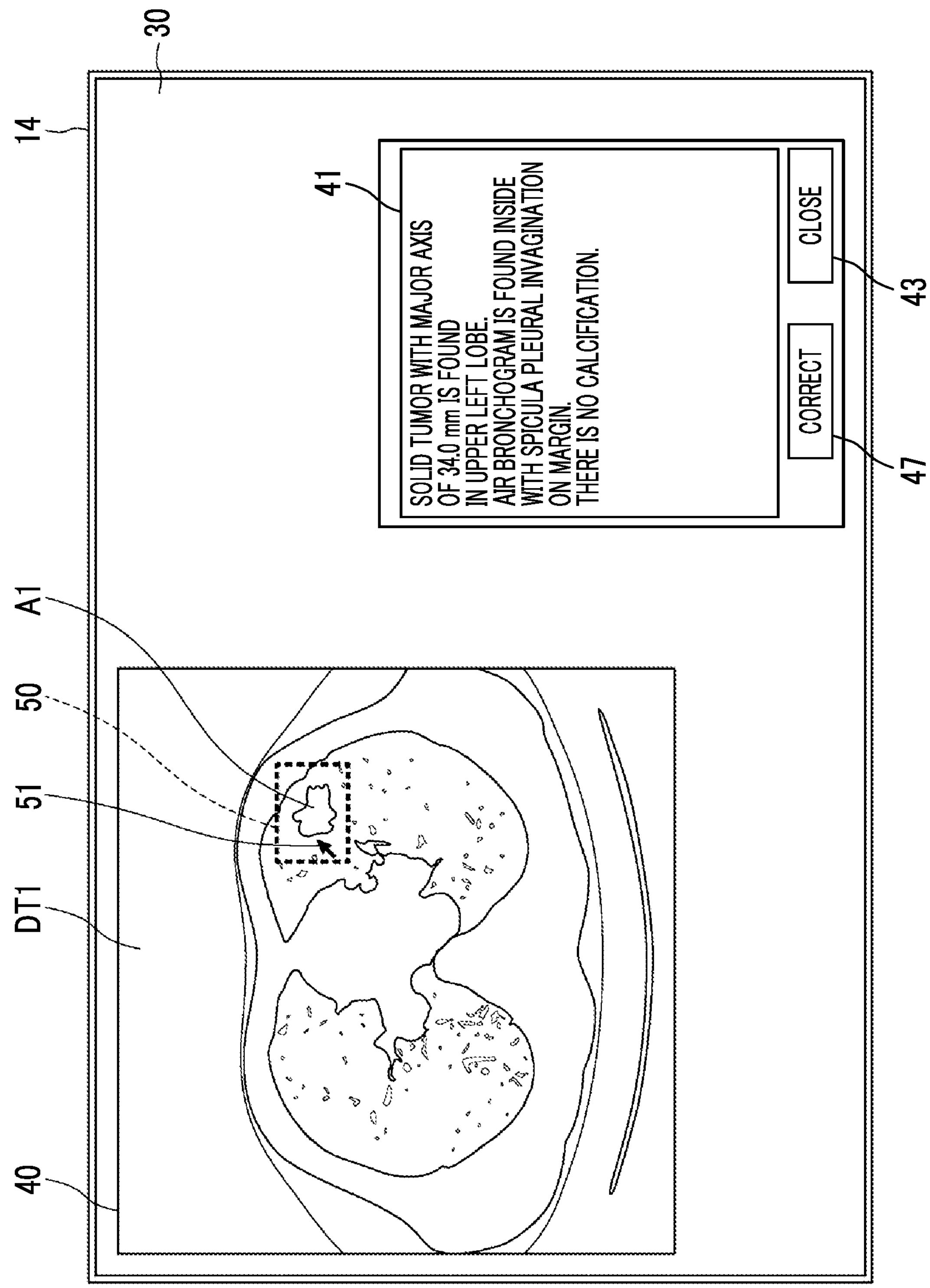
FIG. 14 is a diagram showing a display screen in which only the first display region is displayed.

In the above embodiment, although the first display region 41 and the second display region 42 are displayed at the same time, the present disclosure is not limited thereto. First, as shown in FIG. 14, only the first display region 41 may be displayed. In this case, the close button 43 and a correction button 47 are displayed below the first display region 41. Then, as shown in FIG. 5, the second display region 42 may be displayed only in a case where the operator selects the correction button 47. Thereby, the information displayed in a case where the abnormal shadow is selected can be simplified.

Figure 15:
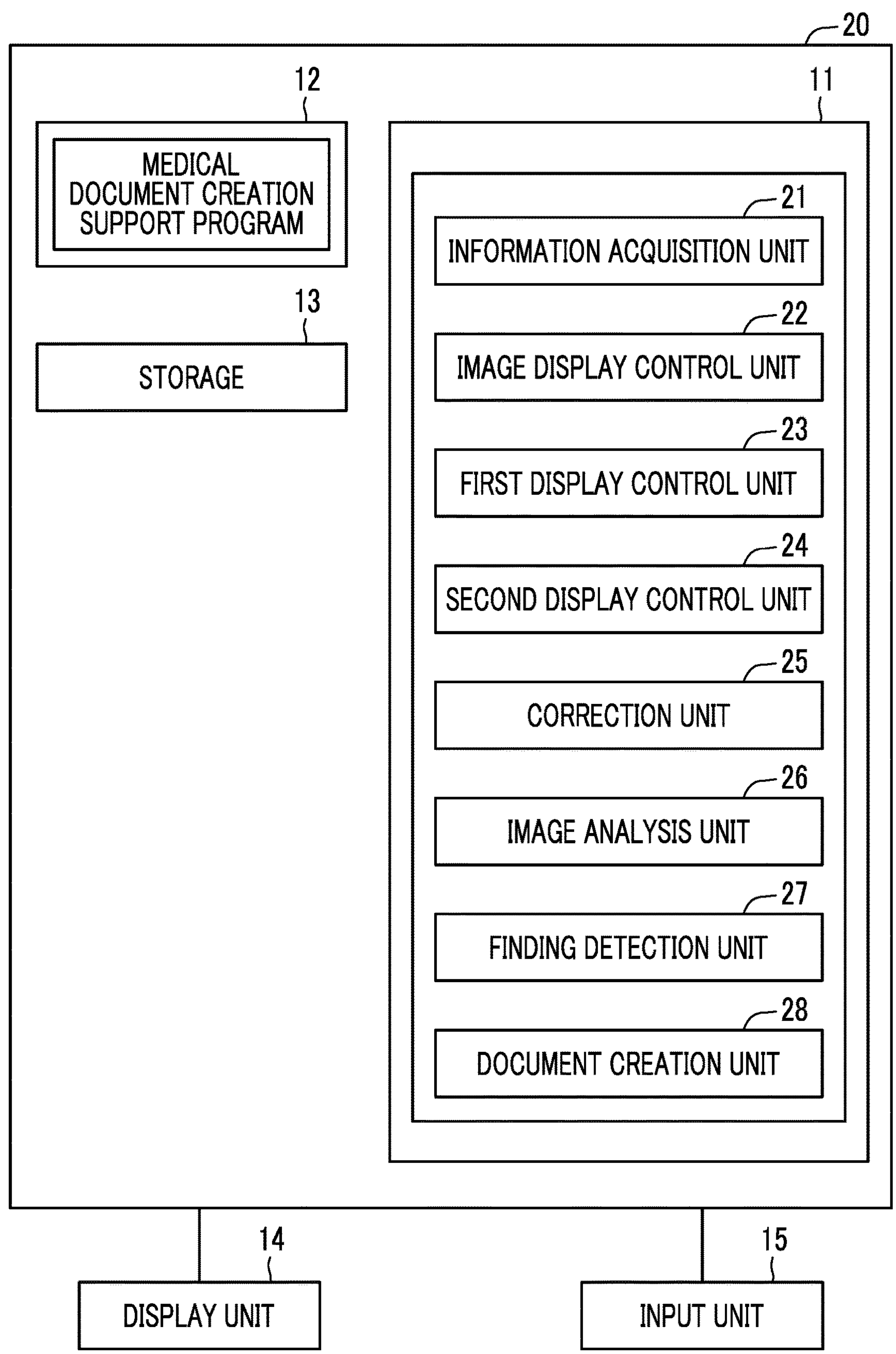
FIG. 15 is a diagram showing a schematic configuration of a medical document creation support apparatus according to another embodiment.

Further, in the above embodiment, although the interpretation WS 3 acquires the interpretation report and the finding information from the interpretation report server 7, the interpretation WS 3 may analyze the medical image to create the finding information and the interpretation report. In this case, as shown in FIG. 15, the medical document creation support program installed on the interpretation WS 3 further defines an image analysis process of analyzing a medical image and detecting an abnormal shadow, a finding detection process of detecting findings about the detected abnormal shadow, and a document creation process of creating an interpretation report using the detected findings. Thereby, the interpretation WS 3 further functions as an image analysis unit 26, a finding detection unit 27, and a document creation unit 28. Further, a program that performs the image analysis process, the finding detection process, and the document creation process may be installed on the interpretation WS 3.

Further, in the above embodiment, although the pull-down menus 45 and 46 are displayed in the case where the findings displayed in the second display region 42 are corrected, the present disclosure is not limited thereto. The findings may be corrected by inputting characters using the input unit 15 for the items of the findings selected in the second display region 42.

Further, in the above embodiment, the interpretation report displayed in the first display region 41 may be corrected by input from the input unit 15. This makes it possible to make minor corrections to the contents of the interpretation report. The characters may be input by voice.

In addition, in the above embodiment, although the present disclosure is applied to the case of creating an interpretation report as a medical document, the present disclosure can also be applied to a case of creating medical documents other than the interpretation report, such as an electronic medical record and a diagnosis report.

Further, in the above embodiment, although the medical document creation support process is performed using a medical image with the diagnosis target as the lung, the diagnosis target is not limited to the lung. In addition to the lung, any part of the human body such as the heart, liver, brain, and limbs can be diagnosed. In this case, the analysis server 9, the image analysis unit 26, the finding detection unit 27, and the document creation unit 28 are prepared to perform an analysis process, a finding detection process, and a document creation process according to the diagnosis target, and select and execute the analysis process, the finding detection process, and the document creation process according to the diagnosis target. Further, the correction unit 25 is also prepared to perform a correction process according to the diagnosis target, and executes the correction process according to the diagnosis target.

Further, in the above embodiment, for example, as hardware structures of processing units that execute various kinds of processing, such as the information acquisition unit 21, the image display control unit 22, the first display control unit 23, the second display control unit 24, the correction unit 25, the image analysis unit 26, the finding detection unit 27, and the document creation unit 28, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (program).

One processing unit may be configured by one of the various processors, or configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units by one integrated circuit (IC) chip as typified by a system on chip (SoC) or the like is used. In this way, various processing units are configured by using one or more of the above-described various processors as hardware structures.

Furthermore, as the hardware structure of the various processors, more specifically, an electrical circuit (circuitry) in which circuit elements such as semiconductor elements are combined can be used.

EXPLANATION OF REFERENCES

1: medical information system
2: modality
3: interpretation workstation
4: medical department workstation
5: image server
6: image database
7: interpretation report server
8: interpretation report database
9: analysis server
10: network
11: CPU
12: memory
13: storage
14: display unit
15: input unit
20: medical document creation support apparatus
21: information acquisition unit
22: image display control unit
23: first display control unit
24: second display control unit
25: correction unit
26: image analysis unit
27: finding detection unit
28: document creation unit
30: display screen
40: image display region
41: first display region
42: second display region
43: close button
44: cancel button
45, 46: pull-down menu of correction candidates
47: correction button
50: rectangular region
51: cursor
A1, A2: abnormal shadow
D1 to Dm, DT1, DT2: tomographic image
G0: medical image

What is claimed is:

1. A medical document creation support apparatus comprising:
- a memory that stores instructions to be executed by a computer, and
- a processor configured to execute the stored instructions,
- wherein the processor displays a medical document including at least one of a plurality of findings indicating features related to abnormal shadows included in a medical image in a first display region on a display screen;

displays a list of the plurality of findings in a second display region on the display screen, which each finding is in a correctable manner; and the medical document comprises a text, corrects the text of the medical document according to a correction instruction for a designated finding in the list of the plurality of findings.

2. The medical document creation support apparatus according to claim 1, wherein the processor further displays a list of correction candidates for the designated finding, and corrects the medical document according to an instruction to select a desired correction candidate in the list of correction candidates.

3. The medical document creation support apparatus according to claim 2, wherein the medical image is a three-dimensional image including a plurality of tomographic images, wherein the processor switches and displays the plurality of tomographic images on the display screen and highlights the abnormal shadow in a case where a tomographic image including the abnormal shadow is displayed during the switching display, displays the first display region in a case where the abnormal shadow is selected in the tomographic image being displayed, and displays the second display region in a case where the abnormal shadow is selected in the tomographic image being displayed.

4. The medical document creation support apparatus according to claim 3, wherein the processor displays the second display region according to an instruction to display the second display region.

5. The medical document creation support apparatus according to claim 4, wherein the processor is further configured to detect the abnormal shadow included in the medical image;

detect the finding included in the abnormal shadow; and create the medical document based on the detected finding.

6. The medical document creation support apparatus according to claim 2, wherein the processor displays the second display region according to an instruction to display the second display region.

7. The medical document creation support apparatus according to claim 6, wherein the processor is further configured to detect the abnormal shadow included in the medical image;

detect the finding included in the abnormal shadow; and create the medical document based on the detected finding.

8. The medical document creation support apparatus according to claim 2, wherein the processor is further configured to detect the abnormal shadow included in the medical image;

detect the finding included in the abnormal shadow; and create the medical document based on the detected finding.

9. The medical document creation support apparatus according to claim 3, wherein the processor is further configured to detect the abnormal shadow included in the medical image;

detect the finding included in the abnormal shadow; and create the medical document based on the detected finding.

10. The medical document creation support apparatus according to claim 1, wherein the medical image is a three-dimensional image including a plurality of tomographic images, wherein the processor switches and displays the plurality of tomographic images on the display screen and highlights the abnormal shadow in a case where a tomographic image including the abnormal shadow is displayed during the switching display, displays the first display region in a case where the abnormal shadow is selected in the tomographic image being displayed, and displays the second display region in a case where the abnormal shadow is selected in the tomographic image being displayed.

11. The medical document creation support apparatus according to claim 10, wherein the processor displays the second display region according to an instruction to display the second display region.

12. The medical document creation support apparatus according to claim 11, wherein the processor is further configured to detect the abnormal shadow included in the medical image;

detect the finding included in the abnormal shadow; and create the medical document based on the detected finding.

13. The medical document creation support apparatus according to claim 10, wherein the processor is further configured to detect the abnormal shadow included in the medical image;

detect the finding included in the abnormal shadow; and create the medical document based on the detected finding.

14. The medical document creation support apparatus according to claim 1, wherein the processor displays the second display region according to an instruction to display the second display region.

15. The medical document creation support apparatus according to claim 14.

wherein the processor is further configured to detect the abnormal shadow included in the medical image;

detect the finding included in the abnormal shadow; and create the medical document based on the detected finding.

16. The medical document creation support apparatus according to claim 1, wherein the processor is further configured to detect the abnormal shadow included in the medical image;

detect the finding included in the abnormal shadow; and create the medical document based on the detected finding.

17. A medical document creation support method comprising:

displaying a medical document including at least one of a plurality of findings indicating features related to abnormal shadows included in a medical image in a first display region on a display screen;

displaying a list of the plurality of findings in a second display region on the display screen, which each finding is in a correctable manner; and the medical document comprises a text, correcting the text of the medical document according to a correction instruction for a designated finding in the list of the plurality of findings.

18. A non-transitory computer readable recording medium storing a medical document creation support program causing a computer to execute a procedure comprising:

displaying a medical document including at least one of a plurality of findings indicating features related to abnormal shadows included in a medical image in a first display region on a display screen;

displaying a list of the plurality of findings in a second display region on the display screen, which each finding is in a correctable manner; and the medical document comprises a text, correcting the text of the medical document according to a correction instruction for a designated finding in the list of the plurality of findings.

* * * * *